United States Patent [19]

Spillman et al.

[11] Patent Number: 4,628,356
[45] Date of Patent: Dec. 9, 1986

[54] DIGITAL X-RAY SCANNER

[75] Inventors: Donald W. Spillman, Aurora; Thomas W. Shilling, Littleton, both of Colo.

[73] Assignee: Imagex, Inc., Aurora, Colo.

[21] Appl. No.: 660,853

[22] Filed: Oct. 15, 1984

[51] Int. Cl.[4] .......................... H05G 1/64; H04N 5/32
[52] U.S. Cl. ...................................... 358/111; 378/99; 378/146
[58] Field of Search .................. 358/111; 378/99, 146, 378/62, 38–40

[56] References Cited

U.S. PATENT DOCUMENTS

| | | | |
|---|---|---|---|
| 3,622,786 | 11/1971 | Walker et al. | 378/99 |
| 3,932,756 | 1/1976 | Cowell et al. | 378/39 |
| 4,160,997 | 7/1979 | Schwartz | 358/111 |
| 4,188,537 | 2/1980 | Franke | 378/146 |
| 4,259,583 | 3/1981 | Albert | 378/99 |
| 4,346,406 | 8/1982 | Kato et al. | 358/111 |
| 4,409,616 | 10/1983 | Ledley | 358/111 |
| 4,413,280 | 11/1983 | Adlerstein et al. | 358/111 |
| 4,444,196 | 4/1984 | Stein | 358/111 |
| 4,472,822 | 9/1984 | Swift | 378/146 |

FOREIGN PATENT DOCUMENTS 0024028 2/1981 European Pat. Off. ............ 378/146

Primary Examiner—Craig E. Church
Assistant Examiner—Charles F. Wieland
Attorney, Agent, or Firm—Burton, Dorr & Carson

[57] ABSTRACT

A digital X-ray scanner device for instantaneously producing an electronic image on a monitor of a object scanned by X-rays. A solid straight electronic linear array is used to detect X-ray shadows and produce an electronic signal which is processed for display. Image enhancement techniques can be utilized including displaying particular windows of the scan data and elimination of background noise and the use of color enhancement. The device can be adapted for retrofitting panoramic dental X-ray scanning machines and other uses such as veterinary scanning and scanning other portions of the human body as well as inanimate objects. Archival storage of the information allows ready access for future use.

8 Claims, 11 Drawing Figures

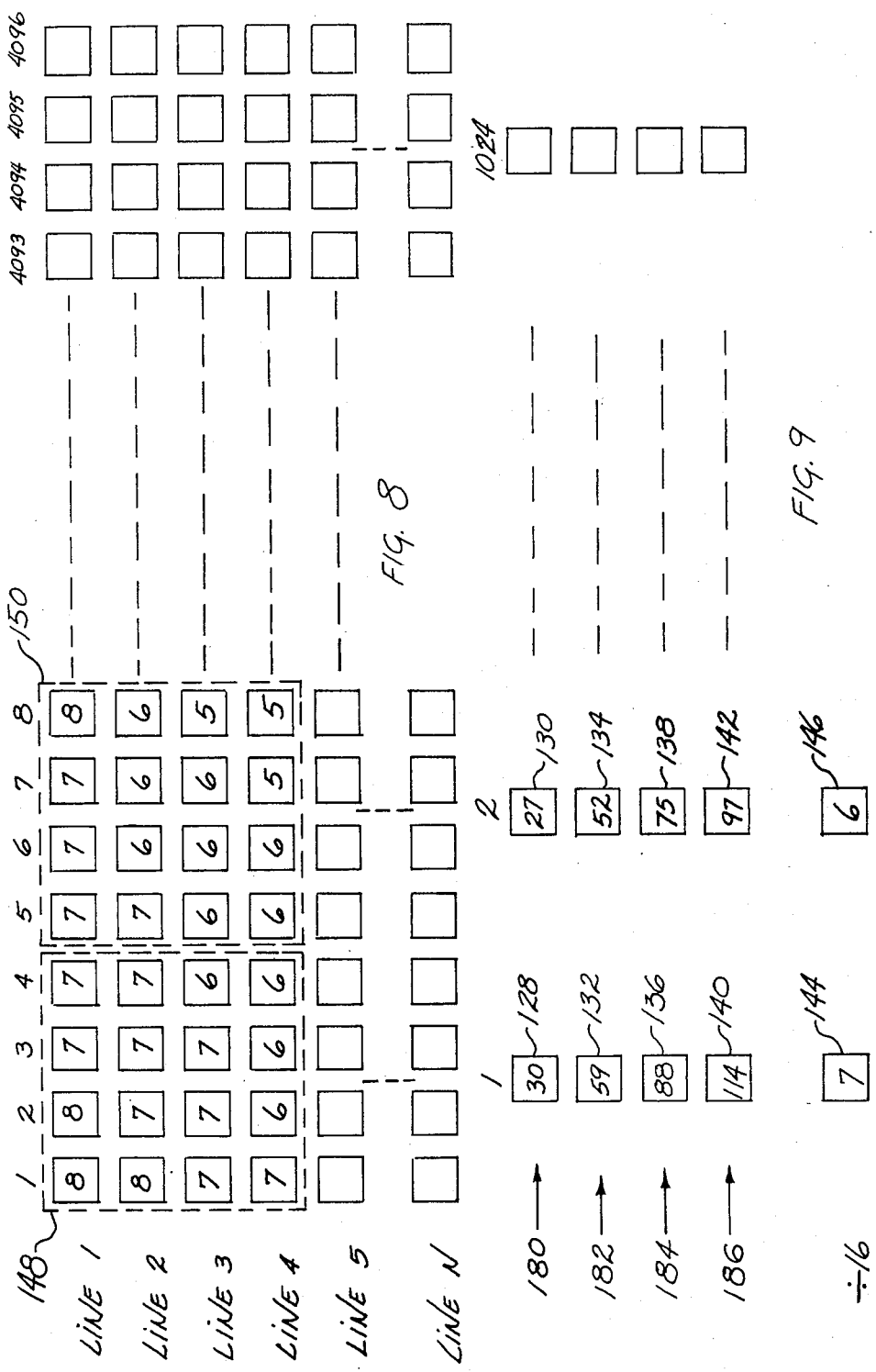

DIGITAL X-RAY SCANNER

BACKGROUND OF THE INVENTION

The present invention pertains generally to X-ray imaging and more particularly to electronic X-ray imaging using electronic transducers.

Current X-ray imaging systems employ the classical configuration of an X-ray source which projects an X-ray beam through an object to produce an X-ray shadow. The X-ray shadow is cast upon standard photographic film. The film is then processed using standard photographic processing techniques to produce an image of the object. This technique has been in common use since the invention of the modern X-ray tube in 1913 and has changed less in fundamental technology than in applications technique. As a result, users of X-ray equipment must still deal with the cumbersome and expensive use of film and film processing to produce X-ray images using the X-ray diagnostic procedure. Millions of dollars are spent each year on film, chemicals and development processor devices which are used in the hundreds of thousands of X-ray machines employed around the world. This conventional process constitutes an archaic manner of capturing, processing and storing X-ray image information.

Various systems have been developed to overcome the problems and costs associated with film processing. For example, U.S. Pat. No. 4,409,616, entitled "Digital Dental System And Method", issued Oct. 11, 1983, to Ledley discloses a system in which an X-ray tube is inserted in the mouth to produce an X-ray beam which penetrates teeth and other hard tissue in the mouth to produce X-ray shadows which impinge upon an image intensifier, such as a fluorescent screen, to produce a visible image of the hard tissue. A TV camera is mounted adjacent the image intensifier to generate an electronic image of the hard tissue. Although such devices overcome the problems associated with film processing, certain disadvantages are inherent in placement of an X-ray tube within the mouth. For example, a certain amount of patient apprehension may result from the fear of excessive X-ray dosage and the inherent danger associated with the high voltages required to activate the X-ray tube within the mouth.

U.S. Pat. No. 3,932,756, issued Jan. 13, 1976, entitled "X-Ray Detector For A Panoramic X-Ray Device" by Cowell et al. discloses an X-ray detector for converting X-ray energy into electrical energy which contains an X-ray sensitive fluorescent screen optically coupled to photovoltaic energy conversion cells. Although the Cowell et al. invention provides the means for electronically imaging X-ray radiation, the sensitivity of photovoltaic energy conversion cells is extremely low and requires large detectors since the sensitivity of the photovoltaic cell is proportional to the surface area of the cell exposed to optical radiation. Consequently, a resolution comparable to that provided by photographic film cannot be achieved using photovoltaic energy conversion cells or photoconductor cells.

U.S. Pat. No. 4,259,583, entitled "Image Region Selector For A Scanning X-Ray System", issued Mar. 31, 1981, to Albert discloses a system in which a scintillator crystal is disposed within the mouth and scans portions of the oral cavity to be imaged. An external X-ray source produces an X-ray beam which penetrates the mouth to produce X-ray shadows which are detected by the scintillator crystal disposed within the mouth. The optical signal produced by the scintillator crystal is then transmitted to a photomultiplier tube or photodiode for conversion into an electrical energy signal. Again, the resolution of such a system is limited by the size of the scintillator crystals. Multiple scintillator crystals provide a non-uniform response such that accurate image data cannot be readily achieved.

U.S. Pat. No. 3,622,785, entitled "Intraoral Minimal Radiation Fluoroscope", issued Nov. 23, 1971 to Irwin et al. discloses a system in which a curved fiber optic bundle is placed within the mouth to detect X-ray radiation produced by an external X-ray source. Phosphor is deposited on the ends of the fiber optic elements to produce optical energy which is transmitted by the fiber optic bundle to an image intensifier to generate a display image. A vidicon tube produces an electronic signal of the display image. A television monitor is used to produce a visual display of the X-ray image. A clear disadvantage of such a system is that the resolution and contrast of the picture obtained is limited by the image retention characteristics of the phosphor, as well as the diameter of the fiber optic cell needed to carry the phosphor. Additionally, the intensity of the image is directly proportional to the size of the phosphor and the attenuation which occurs over the length of the fiber optic cable.

Consequently, prior art methods of attempting to electronically display X-ray radiation image information have been unable to provide resolution comparable to photographic film imaging techniques in a reliable and cost efficient manner.

Other techniques of scanning and signal processing include:

(1) Sonoda, M. S.; Takano, M. S.; Miyahara, M. S.; Kato, M. S.; *Computed Radiography Utilizing Scanning Laser Stimulated Luminescence*, Radiology Vol. 148, No. 3 (September, 1983), (2) *Proceedings Two Dimensional Digital Signal Processing Conference* in Columbia, MO (Oct. 6–8, 1971), (3) Leverenz, *An Introduction to Luminescence of Solids*, RCA Laboratories Division (1950), (4) Aboutalib, Murphy, Silverman *Digital Restoration of Images Degraded by General Motion Blurs*, IEEE Transaction on Automatic Control, Vol. ac-22, No. 3 (June 1977), (5) Cannon, *Blind Deconvolution of Spatially Invariant Image Blurs with Phase*, IEEE Transactions on Acoustics, Speech, and Signal Processing, Vol. ASSP-24, No. 1, (February 1976), (6) Trombka, Seltzer *A Portable X-Ray Imaging System for Small-Format Applications*, Lear Instruments and Methods 158 (1979) 175–180, (7) Gonzalez, Wintz *Digital Image Processing*, Addison-Wesley Publishing Company (1977), (8) Eklundh, Huang, Justusson, Nussbaumer, Tyan, Zohar *Two-Dimensional Digital Signal Processing II, Transforms and Median Filters*, Springer-Verlag (1981), (9) American Science and Engineering, Inc. *MICRO-DOSE Model* 100 *X-Ray Inspection System*

(10) Rozilri, Virai, Hougelot, Driard, *Large Field of View Image Intensifier Gamma Camera Detectors Using a Silicon X Y Scintillation Localizer* Thomson CSF, Boulogne, France,

(11) Yin et al. (Nucl. Methods 158: 175, 1979) which discloses the Lixiscope.

These papers are specifically incorporated herein by reference for all that they disclose.

SUMMARY OF THE INVENTION

The present invention overcomes the disadvantages and limitations of the prior art by providing an X-ray imaging device for electronically detecting and imaging X-ray shadows of an object which uses a linear sensing array, such as a CCD linear array or photodiode linear array, in optical communication with a fluorescent screen to detect X-ray shadows produced by an X-ray beam penetrating the object. The raw image data is then processed and stored to form a series of raster lines which are electronically displayed on a monitor.

The present invention may therefore comprise an X-ray scanning system for producing an electronic image of an X-ray scanned object comprising linear solid state electronic sensing array means for detecting X-ray shadows of an object and producing an analog scan signal representative of the X-ray shadows; means for processing the analog scan signal to produce an analog image display signal suitable for electronic display and a digital scan signal suitable for storage on a digital storage medium; raw data storage means for storing the digital scan signal; monitor means for electronically displaying the analog image display signal; archival storage means for storing the digital scan signal.

The present invention may also comprise an X-ray imaging system for electronically detecting and imaging X-ray shadows of an object comprising X-ray source means for generating a generally rectangularly shaped X-ray beam; scanning means for inducing relative motion between the object and the X-ray beam to produce the shadows of the object; linear photosite detector array means for detecting the X-ray shadows of the object and producing an analog scan signal representative of the X-ray shadows; video digitizing means for producing a digital scan signal in response to the analog scan signal; camera controller means for controlling exposure and clocking of the linear photosite detector array means; raw data storage means for storing digital scan data from the digital scan signal; data formatting means for mapping the digital scan data for storage in the raw data storage means and generating read address signals for reading the digital scan data from the raw data storage means; picture processing means for processing the digital scan data for display; display frame buffer means for storing the digital scan data and generating an analog image display signal monitor means for electronically displaying the analog image display signal.

OBJECTS OF THE INVENTION

It is therefore an object of the present invention to provide an improved X-ray imaging device.

It is also an object of the present invention to provide an X-ray imaging device for electronically detecting and imaging X-ray shadows of an object.

Additional objects, advantages and novel features of the invention are set forth in part in the description which follows and will be understood by those skilled in the art upon examination of the following or may be learned by practice of the invention. The objects and advantages of the invention may be realized and obtained by means of the instrumentalities and combinations particularly pointed out in the appended claims.

BRIEF DESCRIPTION OF THE DRAWINGS

An illustrative and presently preferred embodiment of the invention is shown in the accompanying drawings, wherein:

FIGS. 8 and 9 schematically illustrate the manner in which data is compressed in accordance with the schematic block diagram of FIG. 6.

DETAILED DESCRIPTION OF THE INVENTION

Figure 1:
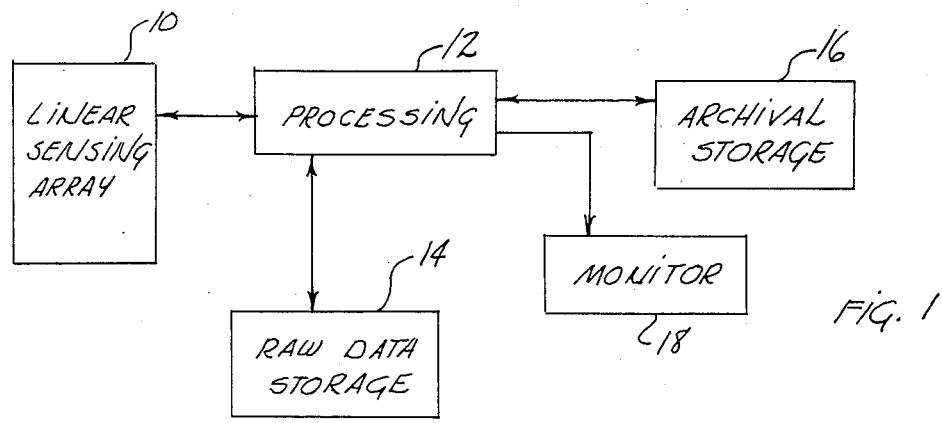
FIG. 1 is a basic schematic block diagram of the device of the present invention.

FIG. 1 comprises a basic schematic block diagram illustrating the functions performed by the device of the present invention. As illustrated in FIG. 1, a linear sensor array 10 for detecting X-ray shadows of an object, such as a linear CCD array, linear photodiode array or other solid state photosite array is coupled directly to a processing unit 12 which processes data from linear array 10 for storage in raw data storage device 14 and archival storage device 16, and for display on a video monitor 18.

Figure 2:
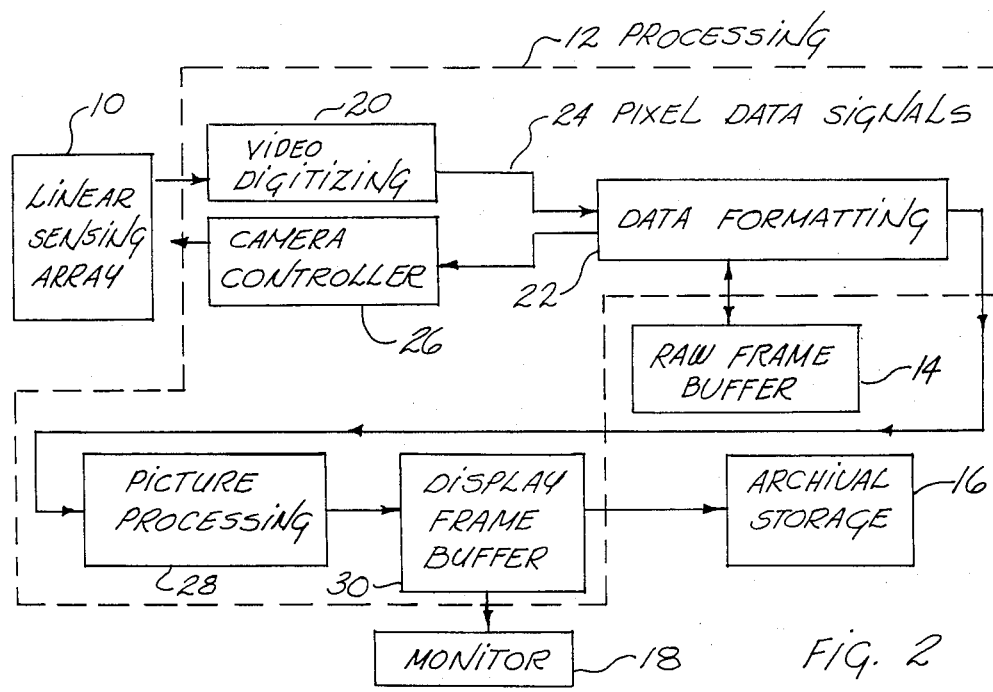
FIG. 2 is a more detailed schematic block diagram of the device of the present invention.

FIG. 2 is a more detailed block diagram of the device of the present invention illustrated in FIG. 1. Linear array 10 is connected to the processing module which comprises various elements as illustrated in FIG. 2. The pixel data signals representing picture element signals produced by the sensor array 10 comprise analog video signals which are converted to a digital signal in a high speed analog to digital converter 20. The digitized video signals comprise pixel data signals 24 which are fed from the analog to digital converter 20 to a data formatting device. Camera controller 26 produces camera control signals to control both the exposure and output timing of the sensing array 10. Line synchronizing pulses are also generated by camera controller 26 to indicate the end of a line of scan data, i.e., the end of a raster line.

Data formatting device 22 functions to format the raw pixel data received from the analog to digital converter 20 to accommodate and map the pixel data signals for storage in raw frame buffer 14 and provide pixel data in a proper format for picture processing device 28.

Picture processing device 28 is capable of performing one or more of several picture processing functions prior to display on monitor 18. The pixel data may be altered in a number of ways including a two dimensional 4 to 1 data compression to allow a single display of the entire image on the monitor, selection of a window of data to provide for an exploded view of a selected portion of the scanned image and application of various image enhancement algorithms such as the elimination of background noise and color enhancement of various shades of the image.

The science of image processing is an extremely mature science with a wealth of techniques for enhancing an image. The present invention, for the first time, allows dental imaging to utilize the vast techniques of image enhancement. The overall goals of image processing in accordance with the present invention are to achieve contrast enhancement, noise reduction, edge sharpening, and improvements in spatial resolution. Below is only a small sample of the classic methods of image processing. It is meant only to give examples rather than be exhaustive or tutorial.

The processed image can be displayed using linear or nonlinear gray level transformations (see "High Resolution Image Enhancement Techniques" by Hall and Kahveci in Proc. of Two dimensional Signal Processing Conference, pages 1-1-1, 1971) or Pseudo-color transformations (see pages 169-173 of "Digital Image Processing" by Gonzalez and Wintz). For example, a logarithmic grey level transformation more closely follows the response of the human eye and produces a more uniform distribution of levels within the image. This enhances low contrast edges. Pseudo-color encoding produces a larger dynamic range than grey levels since it utilizes color and intensity rather than just intensity. The large dynamic range means that a smaller edge can appear more pronounced.

Local digital filtering involves combining data from nearby picture elements to smooth the noise and/or emphasize certain features. One of the most common of local filters it the Medium filter (see "Medium Filtering: Statistical Properties" by Justusson in Topics in Applied Physics, ed. T. S. Huan, Vol. 43, pages 161, 1981). The medium filter preserves sharp edges while smoothing high frequency noise, e.g., spiky noise.

Other filtering techniques involve calculations that use all (or nearly all) of the picture elements to make a transformation into the Fourier space where certain frequency ranges are modified and then transformed back into an image. The Most common filters are low-pass filter (see Gonzalez and Wintz, pages 139-154) and high-pass filters (Gonzalez and Wintz, pages 161-166). Low-pass filters are useful for smoothing noise and high-pass filters can be used for edge enhancement or image sharpening.

The images produced by a panoramic scanner contain blurring due to residue differential motion of the film and the tooth. Image restoration methods can improve the spatial resolution by removing most of the blurring. The most common techniques employ Wiener filtering or Maximum Entropy (see "Image Enhancement and Restoration" by Frieden in Topics in Applied Physics ed. T. S. Huang, vol. 6, page 179, 1979). Other methods, especially designed for motion blurring can be found in Aboutalib et al. (IEEE trans. Auto. Control ac-22:294, 1977) and Cannon (IEEE Trans. Acoutics, Speech, and Signal Processing assp-24:58, 1976).

The processed image data from picture processing unit 28 is further processed in the display frame buffer which produces a 4 bit binary number signal for each pixel data point comprising an address which is used to access a location in a look-up table having a stored data signal of a predetermined intensity for display on monitor 18.

The display frame buffer has a plurality of planes of storage wherein the location of data on each plane comprises the horizontal and vertical axis of display on monitor 18, while the various planes of storage comprise the intensity of the shade to be displayed on monitor 18. For example, if four planes are used, a 4 bit word can be generated which is capable of displaying sixteen different shades of image intensity. A fifth bit can be used for titling, labeling, and related graphics which is overlayed on the 4 bit image for simultaneous display on monitor 18. The analog signal used to produce the image on monitor 18 is produced by a look-up table which generates the pixel analog signals from address locations which are addressed by the 4 bit data signal produced by the display frame buffer. The look-up table can be programmed to store the video pixel data in accordance with the shading desired on monitor 18.

Archival storage device 16 can comprise any one of a number of storage devices capable of storing a large amount of information such as optical disk storage devices and video tape devices.

Figure 3:
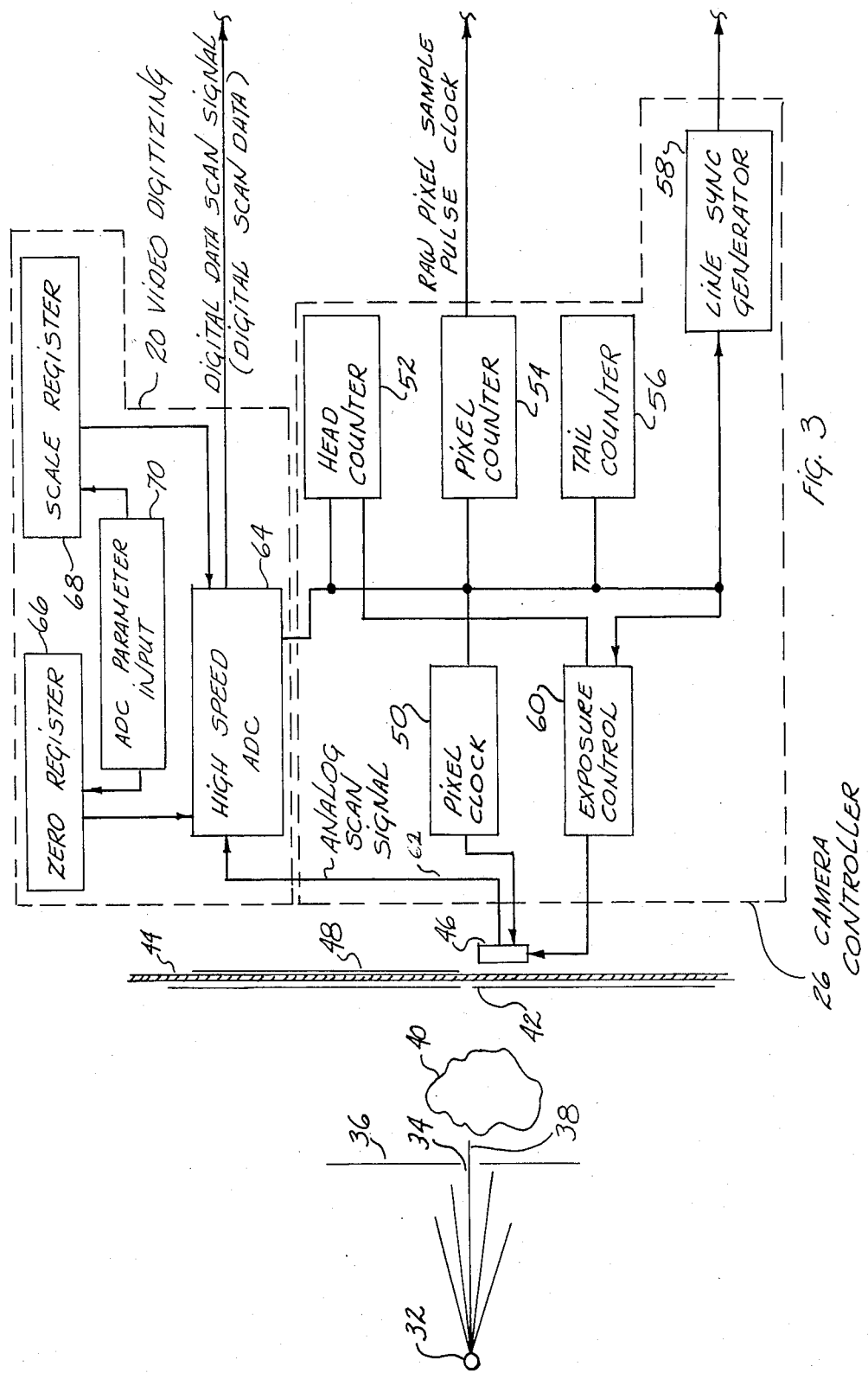
FIG. 3 is a detailed schematic block diagram of the linear sensing array, the video digitizer and the camera controller of the present invention.

FIG. 3 is a schematic block diagram of portions of camera controller 26 and video digitizing module 20. An X-ray point source 32 produces an X-ray beam which impinges upon plate 36 having a slit aperture 34 formed therein. A column beam 38 of X-ray energy is transmitted through slot 34 to penetrate object 40. Object 40 comprises the object to be imaged by the panoramic X-ray machine such, as human teeth, small animals, etc. Object 40 is sequentially scanned by either moving object 40, or by simultaneously moving slit apertures 34 and 42. Inducement of relative motion between X-ray beam 38 and object 40 produces a scanning motion which sequentially exposes object 40 to the rectangularly shaped projection of X-ray radiation. Sensor 46 is placed in a position adjacent slit aperture 42, such that X-ray radiation does not impinge directly upon the sensor array 46. Phosphoric screen 44 moves relative to sensor 46 past slit aperture opening 42 such that X-ray radiation impinging upon fluorescent screen 44 produces an optical response which is sensed by sensor 46. Sensor 46 comprises a linear array aligned in the same direction with slit aperture 42 such that a raster of linear data points is produced by a plurality of sensor elements positioned in a linear array. The transduction material of fluorescent screen 44 can comprise any material capable of producing electromagnetic radiation which can be detected by sensor 46 in response to X-ray radiation. CCD linear arrays, photodiode or other solid state electronic photosite arrays can be utilized which are sensitive to various frequencies of electromagnetic radiation. For example, CCD arrays are sensitive to optical radiation and the visible blue electromagnetic spectral region. Consequently, fluorescent transduction material capable of producing optical radiation in the blue spectral region should be utilized in fluorescent screen 44 when CCD arrays are used in sensor 46. A typical CCD array which can be utilized in accordance with the present invention comprises a Fairchild linear CCD array having 1,024 sensor elements. A Fairchild linear array is also available having 2,048 elements which produces 77 line pairs per millimeter.

The sensing head 46 may be of a movable or stationary type depending upon the particular use or application of the X-ray imaging device. The movable type of X-ray scanning head may be applied to the task of dental diagnostic procedures as well as to other procedures in which the subject is analyzed at a variety of focal planes. Through the use of a relatively stationary positioning of the X-ray beam with respect to a selected focal spot to be imaged, such as a series of teeth, the remaining portion of object 40 comprises a moving background which is not in focus long enough to contribute to the formation of the image so as to effectively smear the non-relevant information such that the non-relevant information appears as background noise. The use of orbital focusing techniques, such as described above, are utilized in panographic X-ray machines and have been applied only with the use of film to produce the X-ray image. The X-ray scanner of the present invention utilizes solid state sensors to obtain diagnostic results to produce an electronic image in a quick and easy fashion which is readily capable of employing image enhancement techniques. Of course, relative motion can be produced between the sensor and the object to be X-ray imaged in any desired fashion. The linear array of sensors 46 scans the X-ray signal to produce a series of image raster lines transverse to the relative movement between the object and the sensing array. The picture size of the image produced by the present invention is the length of the linear array times the number of raster lines produced during the scanning of the image.

Alternatively, spontaneous phosphors can be replaced with stimulated luminescence. Physical processes that involve stimulated emission of photons can have time scale control unlike spontaneously emitting phosphors. The paper entitled "Computer Radiography Utilizing Scanning Laser Stimulated Luminescence" by Sonoda et al. (Radiology, 148:833, 1983) describes such a phosphor. This phosphor includes europium-activated barium fluorohalide compounds such as BaFCl:Eu. After the photostimulable phosphor moves beyond the slit in the detector, a flash of light generated by a stimulation source causes the detector material to phosphor a short time later (7 microseconds). The CCD array is located in a position to record the phosphor emission. Other photostimulable phosphors are also available in addition to the Sonoda et al. phosphor. "An Introduction to Luminescence of Solids" by Leverenz comprises a treatise on various photostimulable phosphors. Many of these phosphors require infrared stimulation and must be maintained at low temperatures and emit with a long time scale. Advantage of the Sonoda et al. technique of photostimulation is that a helium neon laser can be used and the phosphor emission has a short time scale (on the order of microseconds) and the X-ray signal can be stored for periods of at least 8 hours. Implementation of a photostimulable phosphor requires successive exposure of rasters of the phosphor to the X-ray radiation through a slit. Each section of the phosphor must then be stimulated by a helium neon laser or other ultra violet source to cause it to emit. A CCD array can be used or a filter provided which renders the CCD array insensitive to the photostimulation triggering radiation.

Another alternative method of scanning the X-ray radiation is the use of a linear CCD array which is capable of directly detecting the X-ray radiation. X-ray radiation used for medical purposes has an energy level in the 80 Kev region. CCD arrays which are capable of detecting such "hard" radiation are available from Texas Instruments, Inc., Dallas, Tex.

Alternatively, a linear CCD array could be used which is positioned directly in the slit behind the phosphor to directly image the phosphor. An especially etched phosphor could be placed directly on the CCD array to thereby minimize cross-talk and function to protect the array from direct impingement of X-ray radiation. A phosphor having a fast response time and which is capable of stopping the radiation can be deposited directly on the CCD array using various deposition techniques to provide a detector array with high resolution capabilities. Deposition techniques are quite common and can be employed with masks to eliminate cross-talk between adjacent pixel elements of the CCD array.

Another alternative method of scanning the X-ray radiation is to use flying spot scanner techniques. Such techniques are used by American Science and Engineering, Inc., Fort Washington, Cambridge, Mass. in devices such as "Microdose Model 100". Such systems employ a rotating disk with a slit which modulates a fan beam columnator into a moving pencil beam. Such a system can achieve 100 microns spatial resolution. Similar devices can be used in conjunction with a flying spot scanner because of the resolution provided by such a scanning technique.

Camera controller 26 comprises the functional devices as illustrated within the dotted box indicated in FIG. 3. Pixel clock 50 comprises an oscillator for producing data pulse signals at a specified predetermined rate which function as control pulses for the sensing array pixel counter and other data processing clocking pulses. The control pulses from pixel clock 50 are applied to head counter 52, pixel counter 54 and tail counter 56. Head counter 52 provides the timing required to allow all of the leading fill pixels out of the sensing arrays. The leading fill pixels comprise a series of pixels which coordinate the addressing of the raster leading edges. Pixel counter 54 produces a raw pixel sample pulse clock which is used as a timing pulse to gate video image pixels in the hard disk drive multiplexer/demultiplexer 80 within data formatting. Pixel counter 54 provides a head count which is representative of a pixel address within a raster line for each raw pixel sample pulse. The raw pixel sample pulse comprises a clock pulse indicating the presence of a raw pixel data pulse at the output of high speed ADC 64. It functions to synchronize the store/recall mode control device 104 and cue the hard disk controller 108. Tail counter 56 provides an output signal to line sync generator 58 indicating the end of the trailing fill pixels produced by sensing array 46. Line sync generator 58 produces a line synchronization pulse which comprises a marker to identify the end of a stream of video data pixels comprising a raster line. The exposure control device 60 functions to control the integration interval of the sensing array. Exposure control device 60 provides timing to control the movement of image charges within the sensing array such that each time an exposure pulse is generated, the integrated charge of the image is moved to an output shift register such that a new integration interval is initiated. This ensures maximum contrast within the dynamic range of the sensors which is required for further display and processing of the image information. The analog output data produced by the linear sensor array is output on line 62 applied to a high speed analog to digital converter (ADC) 64 comprising a portion of the video digitizing module 20. The high speed ADC 64 functions to convert the analog data produced by sensors 46 to digital data. The high speed ADC 64 must be capable of handling very high data rates, e.g., data rates as high as 8 MHS, since it is the first discrete limiter of the speed at which data coming from the sensing head 46 is processed. A high speed video ADC suitable for use in the present invention comprises an Analog Devices Co. Model #MATV/0820 which is an 8 bit ADC operating at 20 Mhz. The zero register 66 and scale register 68 provide threshold voltages to high speed ADC 64 to control the threshold points for digitizing the analog data. ADC parameter input 70 provides the zero and scale level information representative of the end points of the conversion range of the high speed ADC. The line sync pulses produced by line sync generator 58 are applied to the mapping and control device 72 of FIG. 4. The mapping and control device produces mapping signals comprising address signals for controlling the storage of data on a plurality of random access storage media 74, 76, 78. Random access storage media 74, 76, 78 can comprise any suitable means for storing the data including hard disk drives, such as Winchester disk drives. Control devices such as a hard disk controller are included within the mapping and control device 72 to direct and control the storage and retrieval of data from random access storage media 74, 76, 78. The raw pixel data produced by the high speed ADC of FIG. 3 is applied to the multiplexing controller 80 of FIG. 4. Since both the data rate and data volume of pixel data produced by high speed ADC 64 is extremely high, a plurality of random access storage media 74, 76, 78 may be required. Multiplexing controller 80 directs the pixel data to the plurality of random access storage media such that both the data rate and data volume can be processed by the random access storage media. Multiplexing controller 80 controls the output of pixel data 82 and clock output 84.

To determine the data volume and data rate of pixel data produced by the present invention, the scan area of the sensors can be analyzed. For example, if it is assumed that a linear array is used which is 5 inches long having 4,096 sensor elements and a scan is produced over a width of 12 inches such that 819 number of raster lines are produced per inch, the total density of information points is as follows:

Total number of rasters lines=9,828
pixels≃40.3 Mp (4096×9,828)
bits≃161 Mb (assuming each pixel site is analyzed by a 4 bit word)
bytes≃20 Mb (assuming 8 bit bytes are used)

Figure 4:
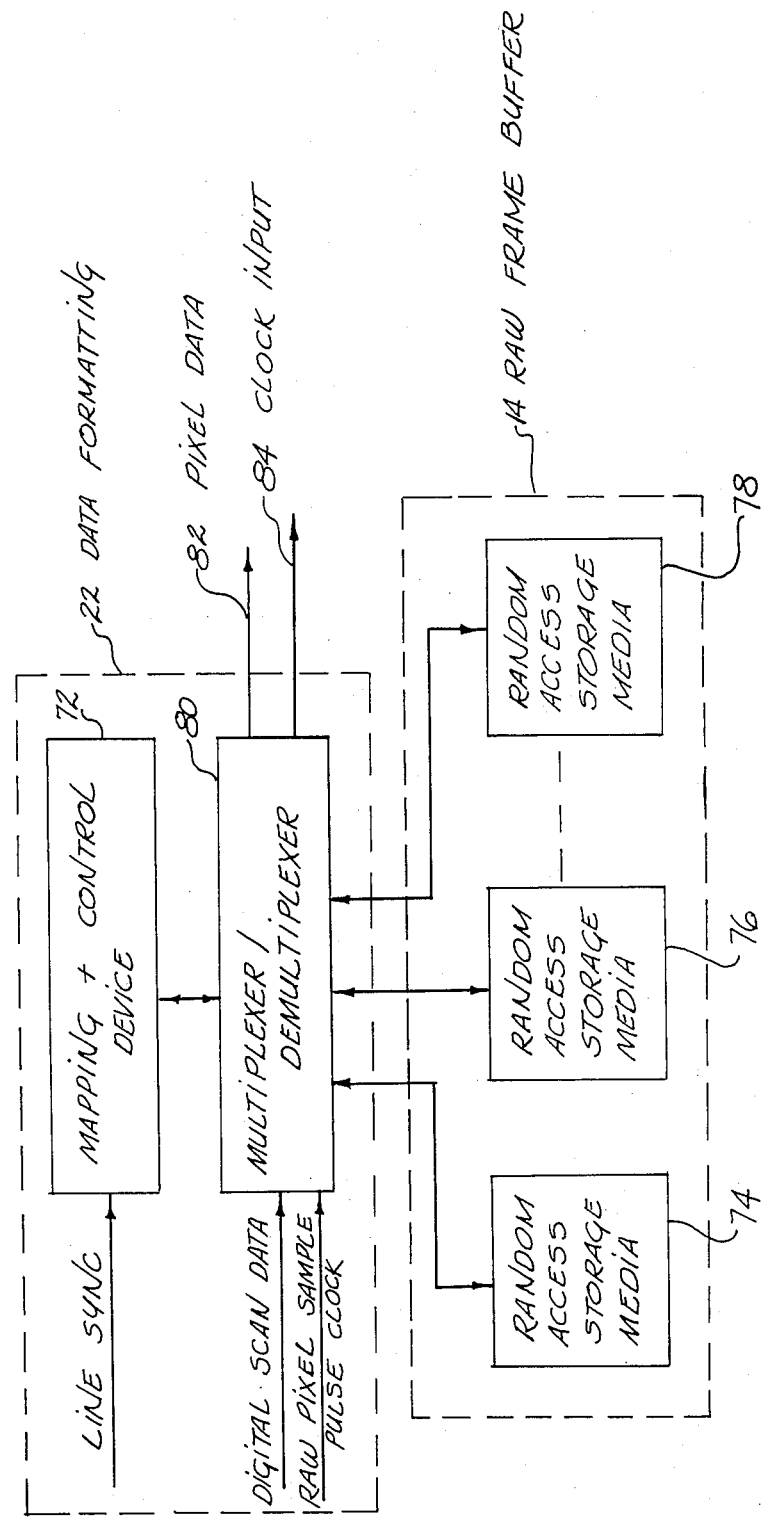
FIG. 4 is a more detailed schematic block diagram of the data formatting and raw frame buffer illustrated in FIG. 2.
Figure 5:
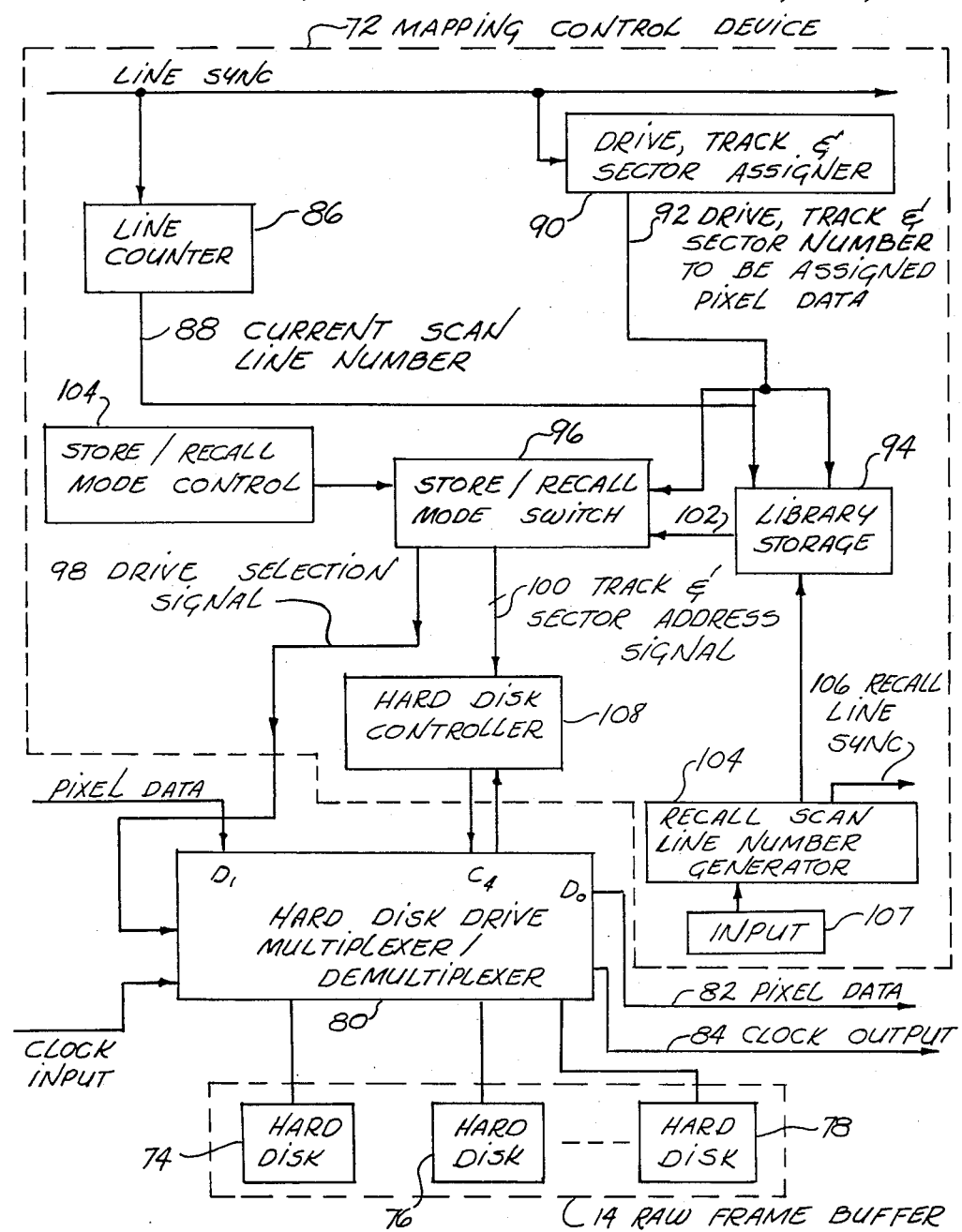
FIG. 5 is a more detailed schematic block diagram of the mapping and control device and raw frame buffer illustrated in FIG. 4.

Typical panoramic X-ray machines produce a scan over a period of approximately 20 seconds. If a standard panoramic X-ray scanning time period is used, the following data rates will be produced for the resolution set forth above:

lines per second≃491
integration time≃0.002 sec.
pixels per second≃2 Mp
bits per second≃8 Mbits
bytes per second≃1 Mbyte FIG. 5 is detailed schematic block diagram of the device of FIG. 4. The mapping and control device 72 receives the line sync signal which is applied to a line counter 86. Line counter 86 provides an output signal 88 representative of the current scan line number. The line sync signal is also applied to a drive, track and sector assignor 90 which produces a drive, track and sector number to be assigned to the pixel data. The drive, track and sector assignor keeps a library of media storage location points which comprise address locations on the storage media on which data cannot be stored because of damage to the storage media. The drive, track and sector assignor does not produce data corresponding to those bad media storage address locations. The drive, track and sector assignor data is stored in library storage device 94 in accordance with an address location comprising the current scan line number 88. The drive, track and sector number signal 92 is also applied to store/recall mode switch 96 which produces separate drive selection signal 98 and track and sector address signals 100. Store/recall mode control device 104 produces a signal to change store/recall mode switch 96 between the store and recall switch positions. In the store position the drive, track and sector number signal 92 is channeled to outputs 98 and 100, while in the recall position, the drive, track and sector number signal is channeled from library storage 94 via input 102 to outputs 98 and 100. Recall scan line number generator 104 produces a series of line number addresses to be outputted from library storage device 94 on output 102 in response to an input signal produced by input 107. Recall scan line number generator 104 also produces a recall line sync number 106 which comprises a line sync signal corresponding to the data produced by recall scan line number generator 104.

Consequently, a drive selection signal 98 and track and sector address signal 100 is produced at the output of store/recall mode switch 96 in response to a real time data scan signal, or, alternatively, a series of drive, track and sector number signals which are stored in library storage device 94 from a previous scan in response to a series of line number address signals produced by recall scan line number generator 104. The track and sector address signals 100 are applied to hard disk controller 108 which comprises a conventional hard disk controller used to control the storage of data on hard disk media such as Winchester disk. Control signals produced by hard disk controller 108 are applied to hard disk drive multiplexer/demultiplexer 80. Drive selection signal 98 is also applied to hard disk drive multiplexer/demultiplexer 80 to control the selection of one of the hard disk drives 74, 76 or 78 within the raw frame buffer 14. The pixel data is also applied to hard disk drive multiplexer/demultiplexer 80 as well as a clock input. The hard disk drive multiplexer/demultiplexer applies the pixel data to one of the hard disk drives 74, 76, 78 in accordance with the drive selection signal 98. Data stored on one of the hard discs 74, 76, 78 in accordance with control signals produced by hard disk controller 108 which assigns address locations for storage of data in accordance with track and sector address signal 100. When store/recall mode switch 96 is in the recall mode, track and sector address signals are applied to hard disk controller 108 to read data from the hard disk selected by drive selection signal 98. Hard disk drive multiplexer/demultiplexer 80 directs the output pixel data along output 82 and output clock signals along clock output 84.

Figure 6:
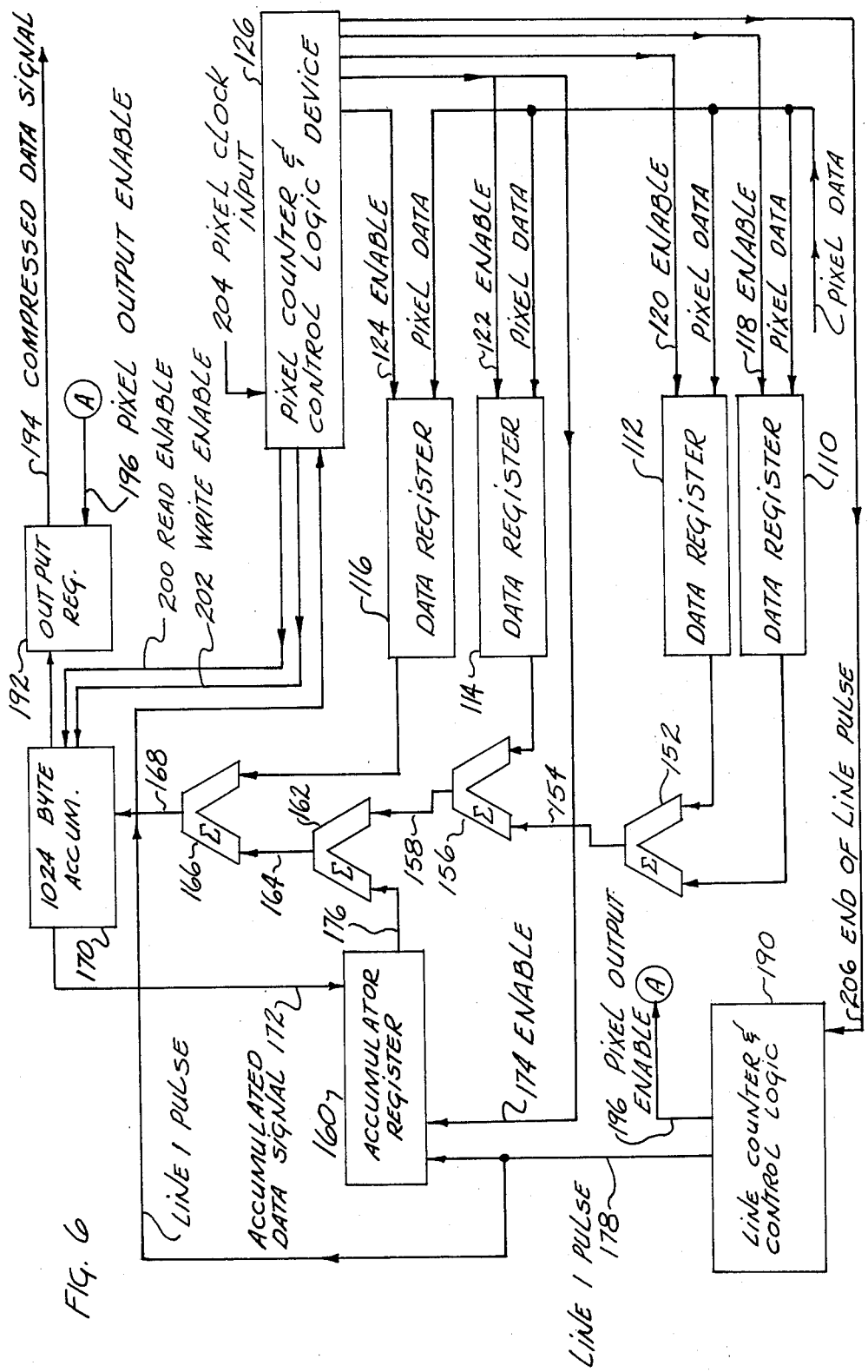
FIG. 6 is a schematic block diagram of the data compression portion of the picture processor of FIG. 2.

FIG. 6 illustrates the data compression function performed by picture processing device 28 illustrated in FIG. 2. The data compression produced by the device of FIG. 6 is a 4:1 two-dimensional compression which reduces the number of pixel data points by a factor of 16. To better understand the operation of the device illustrated in FIG. 6, reference should be made to FIGS. 8 and 9.

FIG. 8 comprises a graphic representation of the pixel data produced in accordance with the present invention. A series of raster lines 1 through n are produced in accordance with the width of the scan generated. In the abovedisclosed example 9,828 raster lines are produced. Each raster line has 4,096 pixel data points produced by 4,096 sensor elements. Referring to line 1, if each of the pixel elements has an intensity represented by the numbers indicated within the pixel element boxes, an accumulation of the first 4 pixel elements of line 1 comprises a single pixel element having an intensity of 30, as represented by pixel element 128 of FIG. 9. The second 4 pixel elements have an accumulated signal of 27 represented by the second pixel element 130 of FIG. 9. In a similar manner, the first 4 pixel elements of line 2 have an accumulated sum of 29, which when added to the accumulated sum of pixel element 128, comprises a pixel element 132 having an accumulated sum of 59. In the same manner, the second 4 pixel elements of line 2 have an accumulated sum of 25, which when added to the accumulated sum of the second 4 pixel elements of line 1, comprise a pixel element 134 having an accumulated sum of 52. Continuing this process, pixel element 136 comprises the accumulated sum of the first 4 elements of lines 1, 2, and 3, while pixel element 138 comprises the accumulated sum of the second 4 pixel elements of lines 1, 2, and 3. Pixel element 140 comprises the accumulated sum of all of the first 4 pixel elements in lines 1 through 4, while pixel element 142 comprises the accumulated sum of all of the second 4 pixel elements of lines 1 through 4. If the accumulated sum of pixel element 140 is divided by 16 and rounded off to the next lowest integer, a single pixel element 144 is produced having an intensity representative of all of the 16 pixel elements within box 148. In a similar manner, pixel element 146 has an intensity representative of all of the pixel elements within box 150. In this manner, a series of pixel elements is produced which comprises a 4 by 4 compression of the pixel element data. This process is continued for the third through 1,024 set of 4 pixel elements and lines 5 through n to generate a matrix of compressed data. The purpose for generation of a matrix of compressed data is to allow display of the entire image on a single cathode ray tube monitor.

The device of FIG. 6 performs the functions represented in FIGS. 8 and 9. Pixel data from pixel data output 82 is applied to each of the registers 110, 112, 114, 116. Enable signals are generated by pixel counter and control logic device 126 to sequentially enable registers 110, 112, 114, 116 such that sequential bits of pixel data are fed in a sequential manner to the data registers. In other words, as represented in FIG. 8, the first pixel data element of line 1 is stored in data register 110, while the second pixel data point is stored in register 112, the third in register 114, and the fourth in register 116. High speed adder 152 sums the value of the first two pixel elements and produces an output 154 representative of the accumulated sum. That number is added to the value of pixel data stored in data register 114 by high speed adder 156. Consequently, the output of high speed adder 156 is a number representative of the first three pixel data points of line 1. This number is added to the number provided by accumulator register 160 and high speed adder 162. The value of accumulator register 160 and the first pass through is zero. The output of high speed summer 162 is applied to high speed summer 166 by way of output 164 which, on the first pass through, sums the value of the first three pixel elements of line 1 with the value of the fourth pixel element provided from register 116.

Consequently, the output of high speed adder 166 comprises a data signal representative of the accumulation of pixel data points 1 through 4 of line 1 which is stored in the first address position of the 1,024 byte accumulator. This accumulated data signal which is the sum of the first 4 pixel signals of line 1, is represented by pixel element 128 of FIG. 9. In a similar manner, the second 4 pixel elements of line, i.e., pixel elements 5 through 8, are added together in high speed adders 152, 156, 162, 166 for storage in the second address position of 1,024 byte accumulator 170, which is represented by pixel element 1,300 of FIG. 9. All of the 4,096 pixel elements are accumulated in four block elements and stored in the 1,024 byte accumulator address positions of 1,024 byte accumulator 170. For the first line, the output of 176 applied to high speed adder 162 from accumulator 160 is zero. The first line pulse 178 produced by line counter and control logic device 180 is applied to the accumulator register 160 to ensure that the output of accumulator register 160 is zero for the first line.

Similarly, line counter and control logic 180 produces a pulse at the beginning of each fourth line, i.e., line 1, line 5, line 9, line 13, line 17, etc., which can be considered to be a "clear pulse" such that the output 176 of the accumulator register 160 is zero during the summing process of each of those lines. At the beginning of line 2, data is written into registers 110, 112, 114, 116 in the same manner as data from line 1 and summed together in the same manner as line 1. However, the first 4 pixel elements of line 1 (represented by pixel element 128, FIG. 9), which is stored in the first address location of 1,024 byte accumulator 170, is loaded into accumulator register 160. Enable pulse 174 causes the output of accumulator register 160 to be applied to high speed adder 162 so that the first 3 pixel elements of line 2 are added to the sum of the first 4 pixel elements of line 1. The fourth pixel element of line 2 is added to the sum of the first 4 pixel elements of line 1 and the first 3 pixel elements of line 2 to produce an output signal 168 from high speed adder 166 which represents the accumulation of the first 4 pixel elements of line 1 and line 2 (represented by pixel element 132, FIG. 9). This number is then stored in the first address location of 1,024 byte accumulator 170.

This process is repeated for the second 4 pixel elements of line 2 such that the sum of the second 4 pixel elements of line 1 and the second 4 pixel elements of line 2 are stored in the second address location of 1,024 byte accumulator 170 (represented by pixel element 134, FIG. 9). This process is repeated for all of the pixel elements of line 2. The same process is used for the pixel elements of line 3 and 4 so that at the end of the fourth line 1,024 byte accumulator 170 has a series of 1024 numbers corresponding to the pixel elements represented by line 186 of FIG. 9.

Output register 192 stores the highest 4 bits of each 8 bit byte and produces an output signal 194 comprising the 4 highest bits of the 8 bit byte in response to enable pulse 196 produced by line counter and control logic 190. By using the highest 4 bits of each 8 bit byte the output of each address location of 1,024 byte accumulator 170 is divided by 16 and rounded off to the next lowest integer. Consequently, a single number is produced by output register 192 which is representative of the average of the 16 pixel elements which are contained within a 4×4 pixel array, such as array 198. The line 1 pulse 178 is applied to pixel counter and control logic device 126 such that read enable 200 and write enable 202 signals can be produced to read and write information into and from 1,024 byte accumulator 170. Pixel clock input 204 is also applied to pixel counter and control logic device 126 to provide necessary timing for production of enable pulses produced by pixel counter and control logic device 126. End of line pulse 206 is also produced by pixel counter and control logic device 126 and applied to line counter and control logic 190 to indicate the end of each line of pixel data. Line counter and control logic 190 counts four lines of data to produce the line 1 pulse 178. The pixel data output signal 194, consequently, comprises a compressed data signal which can be displayed on a monitor so that the entire image can be displayed at one time.

Figure 7:
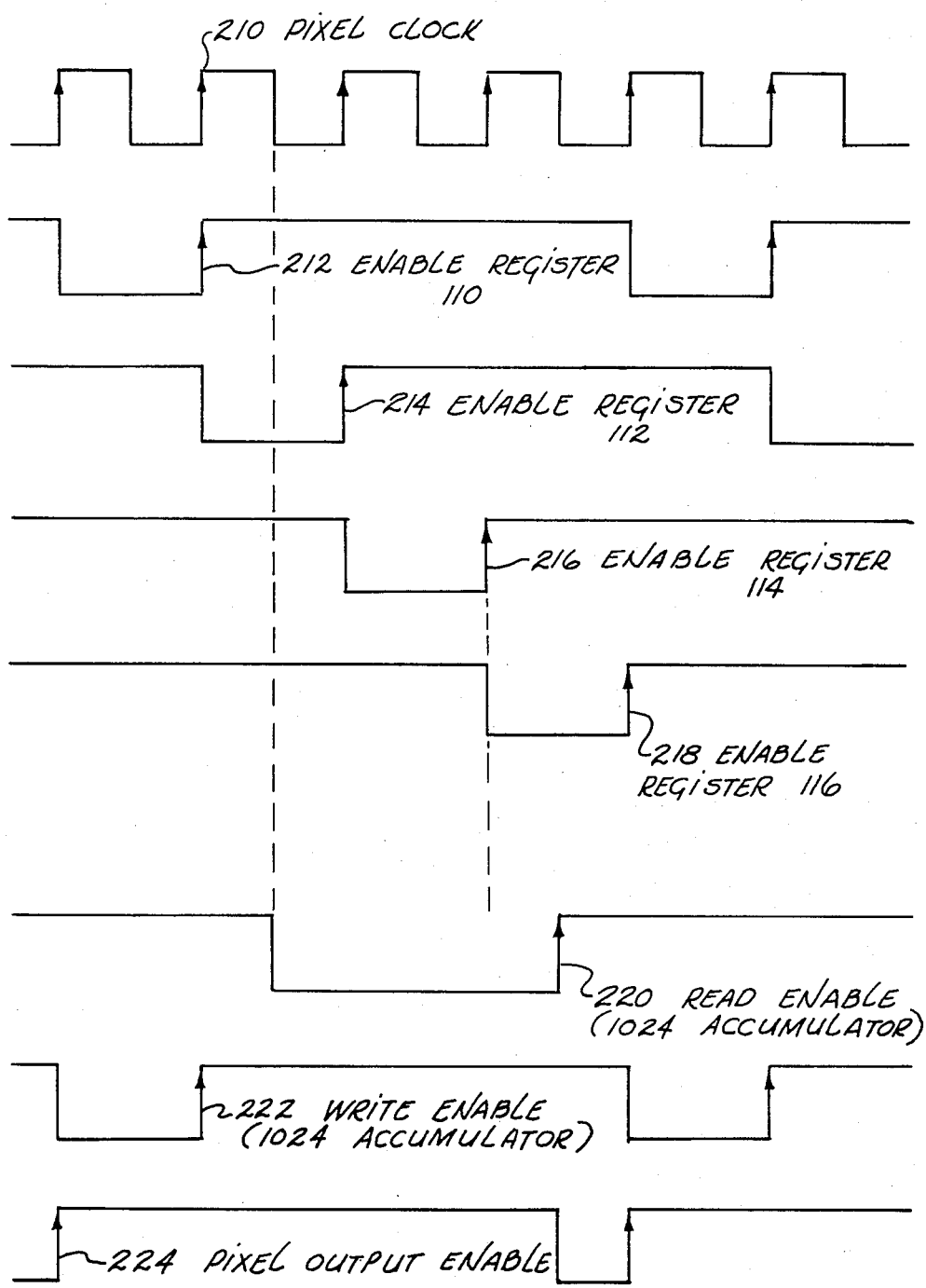
FIG. 7 is a timing chart for signals produced in accordance with the devices illustrated in FIG. 6.

FIG. 7 comprises a pulse diagram of the various signals produced in FIG. 6. Pixel clock signal 210 comprises a series of pixel clock pulses which are triggered on the rising pulse side. Pulse train 212 comprises enable pulses for register 110. Pulse train 214 comprises the enable pulses for register 112. Pulse train 216 comprises the enable pulses for register 114. Pulse train 218 comprises the enable pulses for register 116. Pulse train 220 comprises the read enable pulse produced on output 200 of pixel counter and control logic device 126. Pulse train 222 comprises the write enable pulse produced by pixel counter and control logic device 126. Pulse train 224 comprises the pixel output enable pulse produced at output 196 of line counter and control logic 190.

Figure 10:
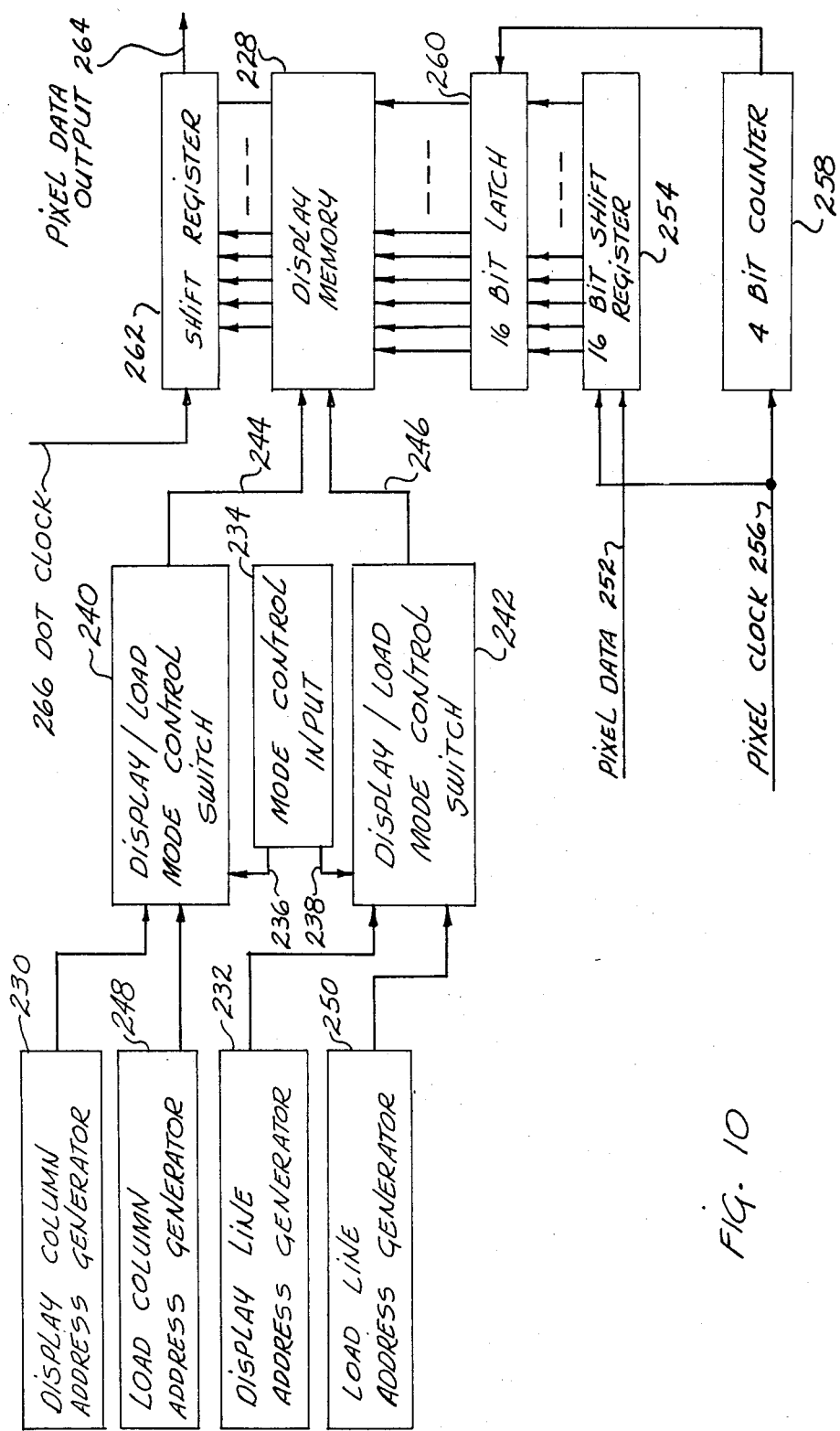
FIG. 10 is a schematic block diagram of a portion of the display frame buffer of FIG. 2.

FIG. 10 comprises a detailed block diagram of a single plane of an image display module contained in display frame buffer 30. As illustrated in FIG. 10, a series of address generators produce address signals which are applied to a display memory 228 to read in or write out information in accordance with the address signal produced. Display column address generator 230 produces a series of column addresses, while display line address generator 232 produces a series of line address signals corresponding to information which is desired to be displayed on monitor 18. In a display mode, mode control input 234 produces output signals 236, 238 which switch display/load mode control switches 240, 242 to the display mode so as to cause display column address signals and display line address signals to be applied to display memory 228 via outputs 244, 246, respectively. In a similar manner, load column address generator 248 and load line address generator 250 produce address signals which are applied to the display memory 228 via display/load mode control switches 240, 242 in response to a mode control signal produced by load control input 234 via outputs 236, 238 to place the display/load mode control switches 240, 242 in the load condition. This allows loading of pixel data into display memory 228, whereas display address generators 230, 232 generate address signals for recalling data for display.

Pixel data 252 is received from picture processing device 28 and fed to a 16 bit shift register 254. Pixel clock data 256 is also applied to 16 bit shift register 254 to clock the pixel data 252 into the shift register in a serial fashion. Four bit counter 258 counts 4 bits of data to unload the 16 bit shift register 254 into 16 bit latch 260. Latch 260 applies the pixel data to the display memory 228 at the address locations generated by the load column address generator 248 and load line address generator 250. Pixel data is read from display memory 228 in response to display column addresses produced by display column address generator 230 and display line address generator 232. This data is unloaded into shift register 262 in a parallel fashion and clocked out at pixel data output 264 in response to DOT clock signal 266. The column and line address generators, as well as the display/load mode control switches and mode control input, control the input and reading out of data from a series of display memories. Each display memory produces a 1 bit binary signal which, in accordance with the preferred embodiment of the invention, is combined with three other 1 bit binary signals produced by three other display memories. This produces a 4 bit binary word capable of indicating 16 different shades of brightness of the pixel data signal for any particular location within the display matrix. An additional display memory can be used to override the image data with other information such as graphic or alpha-numeric information generated in conventional graphic and alpha-numeric generator devices. Alternatively, a 6 bit binary signal can be produced by using 6 display memories. This would provide 64 grey tone levels which clearly eliminates unnecessary quantization noise and increases the effectiveness of image enhancement techniques.

Figure 11:
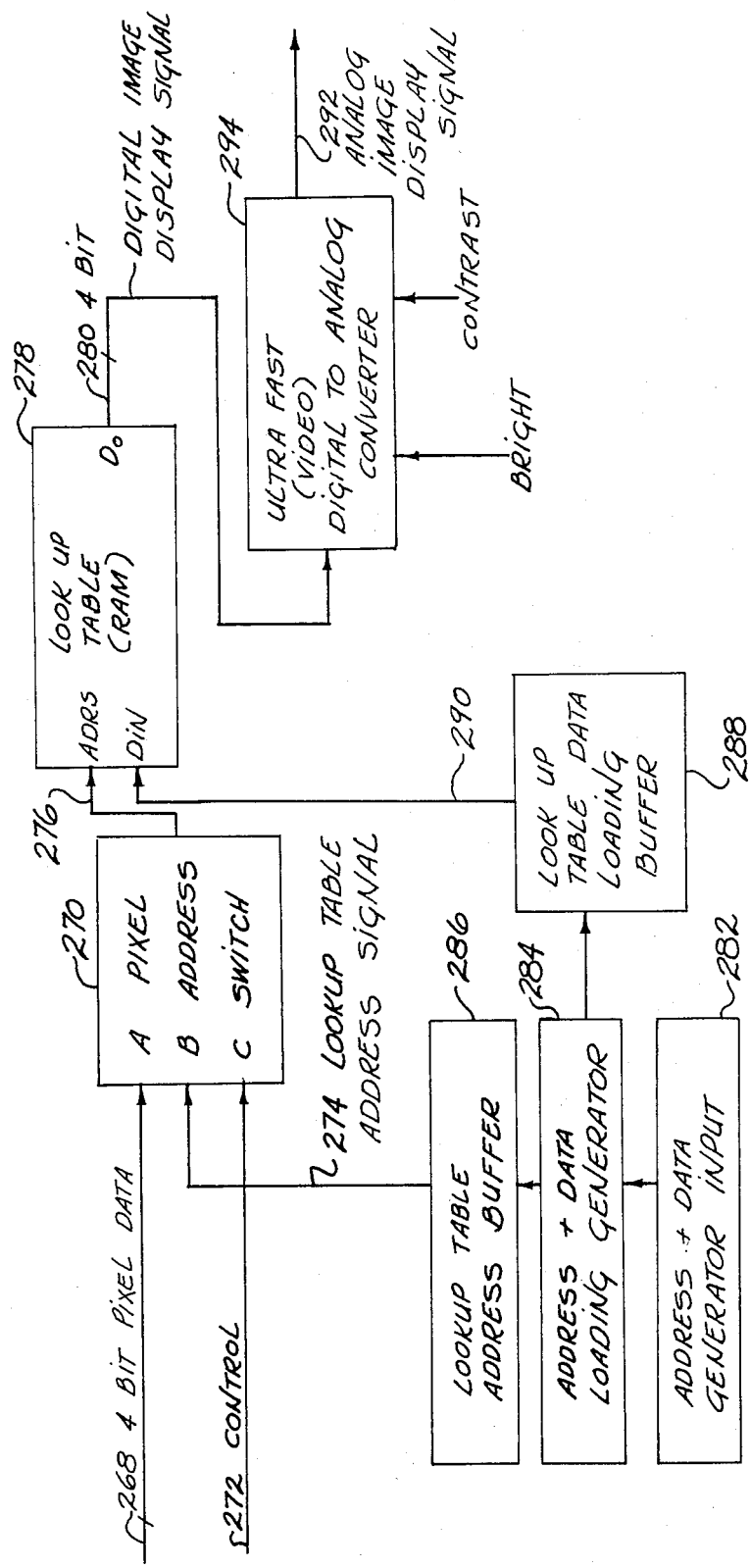
FIG. 11 is a detailed schematic block diagram of an additional portion of the display frame buffer of FIG. 2.

The 4 bit pixel data signal 268 described above, which is generated by four display memory modules 228 is applied to a pixel address switch 270, as illustrated in FIG. 11. Control signal 272 controls the pixel address switch 270 to channel inputs A or B to output 276. The 4 bit pixel data signal 268 and look-up table address signal 274 both comprise address signals which address specified locations within look-up table 278 via input 276. Look-up 278 comprises a data storage device such as a 2K RAM which contains certain stored data having predetermined values in accordance with its address location. Address signal 276 addresses these address locations in look-up table 278 such that look-up table 278 produces an output signal 280 comprising a 4 bit binary word corresponding to the data which is stored at the address location addressed by address signal 276. Address and data generator input 282 generates both data and address signals which are applied to address and data loading generator 284. Address signals generated by address and data loading generator 284 are applied to look-up table address buffer 286, which are applied to the pixel address switch 270 by way of look-up table address signal output 274.

Similarly, data signals generated by address and data loading generator 284 are applied to look-up table loading buffer 288. These data signals are applied to the look-up table 278 by way of output 290 and stored at the address locations produced by the look-up table address signal whenever the pixel address switch 270 is in a condition to load channel B into address input 276. In this manner, data can be loaded into the look-up table 278 according to address locations. The 4 bit data output signal is applied to an ultra fast video digital to analog converter which produces a video analog signal 292 which is applied to monitor 18. Ultra fast video digital to analog converter 294 has control over both the contrast and brightness of the analog video signal 292. In this manner, video analog signals are produced for proper display on the monitor to produce an image of the X-ray data.

Picture processing unit 28 can also perform other functions such as color enhancement and enhancement using various algorithms such as the elimination of background data etc. Image enhancement algorithms constitute conventional methods of processing data for display and can be incorporated in the picture processing device 28 of the present invention utilizing conventional image enhancement picture processing techniques.

Consequently, the present invention provides a device for electronically imaging X-ray image information using a CCD or photodiode linear array in optical communication with a fluorescent screen to detect X-ray shadows produced by an X-ray beam penetrating the object. The image can be produced in a rapid manner and can provide a high resolution data signal in a rapid manner. Image enhancement techniques can be employed which greatly increase the quality of the image over standard film images. Additionally, exploded views of certain portions of the entire image can be displayed on the monitor as well as an overall view. Archival storage of the scan data allows ready access for future use. The data can be stored economically and inexpensively on video tape or video disk. The sensing units can be retrofitted in existing panographic X-ray machines to allow ready conversion of a large capital market. Also, operational costs and processing times are greatly reduced because of the elimination of film and the associated personnel and equipment required to process this film.

The foregoing description of the invention has been presented for the purposes of illustration and description. It is not intended to be exhaustive or to limit the invention to the precise form disclosed, and other modifications and variations may be possible in light of the above teachings. The embodiment was chosen and described in order to best explain the principles of the invention and its practical application to thereby enable others skilled in the art to best utilize the invention in various embodiments and various modifications as are suited to the particular use contemplated. It is intended that the appended claims be construed to include other alternative embodiments of the invention except insofar as limited by the prior art.

What is claimed is:

1. An X-ray imaging system for electronically detecting and imaging X-ray shadows of an object comprising:
    X-ray source means for generating a generally rectangularly shaped X-ray beam;
    scanning means for inducing relative motion between said object and said X-ray beam to produce said shadows of said object;
    linear photosite detector array means for detecting said X-ray shadows of said object and producing an analog scan signal representative of said X-ray shadows;
    video digitizing means for producing a digital scan signal in response to said analog scan signal, said video digitizing means comprising:
      high speed analog to digital converter means for producing said digital scan data in response to said analog scan signal;
      means for setting operational parameters of said high speed analog to digital converter means;
    camera controller means for controlling exposure and clocking of said linear photosite detector array means comprising:
      pixel clock means for generating pixel clock pulses;
      exposure control means for setting the exposure time of said linear photosite detector array means;
      pixel counter means for counting said pixel clock pulses to determine the number of pixels on each raster line;
      line sync generator means for producing a line sync generator pulse at the end of each raster line of pixel data points;
    raw data storage means for storing digital scan data from said digital scan signal;
    data formatting means for mapping said digital scan data for storage in said raw data storage means and generating read address signals for reading said digital scan data from said raw data storage means;
    means for selecting a predetermined window of said raw image data and retrieving said window of data from said storage means for display;
    picture processing means for processing said digital scan data for display comprising:
      data compression means for compressing said digital scan data in two dimensions to increase the amount of said data which can be displayed on a monitor;
      means for processing said digital scan data to enhance an image formed by displaying said digital scan data;
    display frame buffer means generating an analog image display signal comprising:
      display look-up table means for storing said digital scan data in address locations corresponding to the positional location for display of said data on said monitor means and generating a binary signal corresponding to the magnitude of said digital scan data;
      display address generator means for generating address signals of data to be displayed on said monitor means;
      load address generator means for generating load address signals for storage of said digital scan data in said display look-up table means at said address locations corresponding to said positional locations for display of said data on said monitor means;
      digital to analog converter means for generating said analog image display signal;
    monitor means for electronically displaying said analog image display signal.

2. The system of claim 1 wherein said data formatting means comprises:
    drive, track and sector assignor means for generating a drive selector signal for selecting one of said random access storage means for storing a raster line of said digital scan data, for generating a track selector signal for selecting a track for storage on the selected random access storage means and for generating a sector selector signal for selecting a sector for storage on said track selected or said selected random access storage means;
    library storage means for storing said drive, track and sector data generated by said drive, track and sector assignor for each raster line of said digital scan data;
    store/recall mode control switch means for controlling the mode of operation of said data formatting means between writing data into and writing data from said random access storage means;
    recall scan line number generator means for generating line number address signals which are applied to library storage means to indicate the lines of data to be written out from said random access storage means;

disk controller means for controlling the operation of said random access storage means;

multiplexer/demultiplexer means for selecting one of said random access storage means in response to said drive selector signal generated by said drive, track and sector assignor means.

3. The system of claim 1 wherein said data compression means comprises:

a preselected number of data register means for sequentially storing an identical number of pixel elements of said digital scan data to form a plurality of pixel data groups for each raster line of said digital scan data;

high speed adder means for sequentially adding said pixel elements in each pixel data group for storage in a byte accumulator means;

accumulator register means for adding corresponding pixel data groups for each raster line for a preselected number of raster lines equal to said preselected number of said data register means;

output register means for generating a compressed data signal wherein a preselected number of least significant digits is eliminated which is equal to said preselected number of data register means.

4. The system of claim 1 wherein said display look-up table means comprises:

storage means for generating a digital image display signal in response to said binary signal which comprises an address signal for addressing address locations in said storage means wherein digital image display data is stored which has a magnitude corresponding to said address locations.

5. The system of claim 1 further comprising:
archival storage means for storing said analog image display signal.

6. The system of claim 1 further comprising:
archival storage means for storing said digital scan data.

7. The system of claim 1 wherein said picture processing means includes a data compression means comprising:

a preselected number of data register means for sequentially storing an identical number of pixel elements of said digital scan data to form a plurality of pixel data groups for each raster line of said digital scan data;

high speed adder means for sequentially adding said pixel elements in each pixel data group for storage in a byte accumulator means;

accumulator register means for adding corresponding pixel data groups for each raster line for a preselected number of raster lines equal to said preselected number of said data register means;

output register means for generating a compressed data signal wherein a preselected number of least significant digits is eliminated which is equal to said preselected number of data register means.

8. The system of claim 1 wherein said display look-up table means comprises:

storage means for generating a digital image display signal in response to said binary signal which comprises an address signal for addressing address locations in said storage means wherein digital image display data is stored which has a magnitude corresponding to said address locations.

* * * * *